(12) United States Patent
Morein et al.

(10) Patent No.: US 10,729,764 B2
(45) Date of Patent: Aug. 4, 2020

(54) ISCOM PREPARATION AND USE THEREOF

(71) Applicant: Novavax AB, Uppsala (SE)

(72) Inventors: Bror Morein, Uppsala (SE); Karin Lövgren Bengtsson, Uppsala (SE)

(73) Assignee: Novavax AB, Uppsala (SE)

( * ) Notice: Subject to any disclaimer, the term of this patent is extended or adjusted under 35 U.S.C. 154(b) by 1217 days.

(21) Appl. No.: 14/587,116

(22) Filed: Dec. 31, 2014

(65) Prior Publication Data

US 2015/0209425 A1 Jul. 30, 2015

Related U.S. Application Data

(63) Continuation of application No. 10/520,022, filed as application No. PCT/SE03/01180 on Jul. 7, 2003, now abandoned.

(30) Foreign Application Priority Data

Jul. 5, 2002 (SE) .................................... 02021103

(51) Int. Cl.
*A61K 39/39* (2006.01)
*A61K 39/00* (2006.01)

(52) U.S. Cl.
CPC .... *A61K 39/39* (2013.01); *A61K 2039/55577* (2013.01)

(58) Field of Classification Search
None
See application file for complete search history.

(56) References Cited

U.S. PATENT DOCUMENTS

| | | |
|---|---|---|
| 4,900,549 A | 2/1990 | De Vries |
| 5,057,540 A | 10/1991 | Kensil |
| 5,620,690 A | 4/1997 | Kersten |
| 6,231,859 B1 | 5/2001 | Kensil |
| 6,352,697 B1 | 3/2002 | Cox |
| 6,428,807 B1 | 8/2002 | MacFarlan |
| 6,558,670 B1 | 5/2003 | Friede |
| 8,821,881 B2 | 9/2014 | Morein |
| 2006/0121065 A1 | 6/2006 | Morein et al. |
| 2006/0239963 A1 | 10/2006 | Morein |

FOREIGN PATENT DOCUMENTS

| | | |
|---|---|---|
| AU | 2003245220 B2 | 4/2009 |
| CA | 2 491 457 C | 9/2012 |
| EP | 0 109 942 A2 | 5/1984 |
| EP | 0 362 279 B1 | 1/1995 |
| EP | 1 539 231 B1 | 6/2009 |
| WO | 88/09336 A1 | 12/1988 |
| WO | 90/03184 A1 | 4/1990 |
| WO | 96/11711 A1 | 4/1996 |
| WO | 97/30728 A1 | 8/1997 |
| WO | 98/36772 A1 | 8/1998 |
| WO | 2004/004762 A1 | 1/2004 |
| WO | 2005/002620 A1 | 1/2005 |

OTHER PUBLICATIONS

Ronnberg et al., "Adjuvant activity of non-toxic Quillaja saponaria Molina components for use in ISCOM matrix," Vaccine, vol. 13, No. 14, pp. 1375-1382 (1995).
International Search Report issued in Application No. PCT/SE03/01180 dated Oct. 9, 2003.
Written Opinion issued in Application No. PCT/SE2004/001038 dated Nov. 1, 2004.
International Search Report issued in Application No. PCT/SE2004/001038 dated Nov. 1, 2004.
Notice of Allowance issued in Canadian Patent Application No. 2,491,457 dated Feb. 21, 2012.
Submission in response to Report No. 1 regarding Australian Patent Application No. 2003245220 dated Feb. 24, 2009.
Office Action issued in Canadian Patent Application No. 2,491,457 dated Aug. 9, 2010.
Communication pursuant to Article 96(2) EPC issued in European Patent Application No. 03 738 849.3, dated Mar. 1, 2007.
Notice of Reason for Rejection issued in Japanese Patent Application No. 2004-519469 dated May 24, 2010.
Notice of Reason for Rejection issued in Japanese Patent Application No. 2004-519469 dated Nov. 13, 2009.
"Adjuvanting Viral vectored Malaria Vaccines With Matrix M" ClincialTrials.gov Identifier NCT01669512, U.S. National Institutes of Health; available at http://clinicaltrials.gov/ct2/show/NCT01669512?term=Matrix-M+or+Matrix+M&rank=1, Mar. 9, 2014, pp. 1-4.
Cox et al., "Prospects for the Development of New Vaccine Adjuvants", BioDrugs, vol. 12(6), pp. 439-453 (1999), Adis International Limited.
Cox et al., "Development of an Influenza-ISCOM Vaccine", Vaccine Design (eds. G. Gregoriadis et al. ), Springer Science + Business Media, New York (1997), pp. 33-49.
Coulter et al., "Studies on experimental adjuvanted influenza vaccines: comparison of immune stimulating complexes (Iscoms) and oil-in-water vaccines", Vaccine, vol. 16, No. 11/12, pp. 1243-1253 (1998), Elsevier Science Ltd., Great Britain.
McKenzie et al., "ISCOMATRIX vaccines: Safety in human clinical studies", Human Vaccines, vol. 6, No. 3, pp. 237-246 (2010), Landes BioScience.
"Safety and Immunogenicity Study of Therapeutic HSV-2 Vaccine", ClinicalTrials.gov Identifier NCT01667341, U.S. National Institutes of Health; available at http://clinicaltrials.gov/ct2/show/NCT01667341?term=matrix+m&rank=3, Mar. 9, 2014, pp. 1-4.

(Continued)

*Primary Examiner* — Terry A McKelvey
*Assistant Examiner* — Catheryne Chen
(74) *Attorney, Agent, or Firm* — Cooley LLP

(57) ABSTRACT

The invention relates to a composition comprising a mixture of at least two iscom complexes each complex comprising essentially one saponin fraction from *Quillaja Saponaria* Molina. The complexes may be iscom complexes or iscom matrix complexes. The invention also pertains to the use of such a mixture for the preparation of an immunomodulating pharmaceutical, and adjuvant, formulations for immunization, e.g. for production of monoclonal antibodies, and a vaccine. Kits of parts comprising at least two parts, wherein each part comprises one iscom complex or one iscom matrix complex according to the invention are also embraced.

26 Claims, 5 Drawing Sheets

(56) References Cited

OTHER PUBLICATIONS

Bengtsson et al., "Matrix-M adjuvant increases immunogenicity of seasonal influenza vaccine for the elderly", manuscript in preparation, pp. 1-27(2014).
Wald "A Novel Therapeutic Vaccine (GEN003) for Genital Herpes Reduces HSV-2 Shedding: Initial Results of Clinical Trial GEN003-001", Presented at Interscience Conference on Antimicrobial Agents and Chemotherapy (ICAAC 2013), Denver, CO. Sep. 12, 2013, pp. 1-21.
Magnusson et al., "Matrix-M adjuvanted envelope protein vaccine protects against lethal lineage 1 and 2 West Nile virus infection mice", Vaccine vol. 32, pp. 800-808 (2014), Elsevier Ltd.
Fossum et al., "Early inflammatory response to the saponin adjuvant Matrix-M in the pig", Veterinary Immunology and Immunopathology, http://dx.doi.org/10.1016/j.vetimm,2013.07.007(2013), pp. 1-9, Elsevier B.V.
Magnusson et al., "Immune enhancing properties of the novel Matrix-M adjuvant leads to potentiated immune responses to an influenza vaccine in mice", Vaccine, http://dx.doi.org/10.1016/j.vaccine.2013.01.039(2013), pp. 1-9, Elsevier Ltd.
Skoberne et al., "An adjuvanted herpes simplex virus 2 subunit vaccines elicits a T cell response in mice and is an effective therapeutic vaccine in Guinea pigs", Journal of Virology. vol. 87, pp. 3930-3942 (2013).
Ahlberg et al., "Global transcriptional response to ISCOM-Matrix adjuvant at the site of administration and in the draining lymph node early after intramuscular injection in pigs", Developmental and Comparative Immunology, vol. 38, pp. 17-26 (2012), Elsevier Ltd.
Pedersen et al., "Matrix-M adjuvanted virosomal H5N1 vaccine confers protection against lethal viral challenge in a murine model", Influenza and Other Respiratory Viruses. DOI:10.1111/j.1750-2659.2011.00256.x(2011), pp. 1-12, Blackwell Publishing Ltd.
Sjolander et al., "Uptake and adjuvant activity of orally delivered saponin and ISCOM vaccines", Advanced Drug Delivery Reviews, vol. 34, pp. 321-338 (1998), Elsevier Science B.V.
Lovgren-Bengtsson, "6 Preparation and Use of Adjuvants", Methods in Microbiology, vol. 25, pp. 471-502 (1998), Academic Press Ltd.
Kensil, "Saponins as Vaccine Adjuvants", Critical Reviews in Therapeutic Drug Carrier Systems, vol. 13(1&2), pp. 1-55 (1996), Begell House Inc.
Sjolander et al., "ISCOMs: an adjuvant with multiple functions", Journal of Leukocyte Biology, vol. 64, pp. 713-723 (1998).
Boulter et al., "Evaluation of recombinant sporozoite antigen SPAG-1 as a vaccine candidate against Theileria annulata by the use of different delivery systems", Tropical Medicine and International Health. vol. 4, pp. A71-A77 (1999), Blackwell Science, Ltd.
Rimmelzwaan et al., "A randomized, double blind study in young healthy adults comparing cell mediated and humoral immune responses induced by influenza ISCOM vaccines and conventional vaccines", Vaccine, vol. 19, pp. 1180-1187 (2001), Elsevier Science Ltd.
Wald et al., Novel Therapeutic Vaccine for Genital herpes Reduces Genital HSV-2 Shedding in ICAAC 2013, Denver, CO, Sep. 2013, cover page and p. 219, Abstract 183 (G).
Genocea Biosciences, Genocea Reports Positive Initial Phase 1/2A Results for GEN-003, It's Pioneering Therapeutic Vaccine Candidate for the Treatment of Herpes Simplex Virus-2 (HSV-2), at ICAAC 2013, press release, Cambridge MA, Sep. 12, 2013, pp. 1-3.
Cox et al., "Evaluation of virosomal H5N1 vaccine formulated with Matrix M adjuvant in phase I clinical trial", . Vaccine, Elsevier Ltd, vol. 29, pp. 8049-8059, Aug. 22, 2011.

Pedersen, et al., "T-Helper 1 Cells Elicited by H5N1 Vaccination Predict Seroprotection", Journal of Infectious Disease, 206, pp. 158-166, Jul. 15, 2014.
Certificate of Patent for Japanese Patent No. 4636877, Application No. 2004-519469, Registration Date Dec. 3, 2010.
Barr et al., "ISCOMs and other saponin based adjuvants", Advanced Drug Delivery Reviews, (1998), 32: 247-271.
Ozel et al., "Quaternary Structure of the Immunostimulating Complex (Iscom)", Journal of Ultrastructure and Molecular Structure Research, (1989), 102: 240-248.
Lucy et al., "Structure and Assembly of Macromolecular Lipid Complexes Composed of Globular Micelles", Journal of Molecular Biology, (1964), 8: 727-748.
Nord et al., "Novel acetylated triterpenoid saponins in a chromatographic fraction from Quillaja saponinaria Molina", 2000, Carbohydrate Research, 329: 817-829.
Eyles et al., "Immunodominant Francisella tularensis antigens identified using proteome microarray", Proteomincs, 2007, pp. 2172-2183.
Lavelle et al. "Cholera Toxin Promotes the Induction of Regulatory T Cells Specific for Bystander Antigens by Modulating Dendritic Cell Activation." The Journal of Immunology, (2003), 171: 2384-2392.
Drane et al. "Iscomatrix Adjuvant for Prophylactic and Therapeutic Vaccines", Experts Rev. Vaccines, 6(5), (2007), pp. 761-772.
Morein et al. "Current Status and Potential Application of ISCOMs in Veterinary Medicine." Advanced Drug Delivery Reviews, 56 (2004), pp. 1367-1382.
Johansson et al. "Iscoms with Different Quillaja Saponin Components Differ in Their Immunomodulating Activities." Vaccine, 17 (1999), pp. 2894-2900.
"Committee for Veterinary Medicinal Products, Quillaia Saponins, Summary Report", The European Agency for the Evaluation of Medicinal Products, EMEA/MRL/055/95-FINAL, Feb. 1996, pp. 1-2.
"Safety Evaluation of Certain Food Additives and Contaminants Quillaia Extracts," WHO Food Additives Series:48, 2002.
Behboudi et al. "Quillaja Saponin Formulations that Stimulate Proinflammatory Cytokines Elicit a Potent Acquired Cell-Mediated Immunity." Scandinavian Journal of Immunology, 50 (1999), pp. 371-377.
Ekstrom et al. "Iscom and Iscom-Matrix Enhance by Intranasal Route the IgA responses to OVA and rCTB in local and remote muscosal secretions." Vaccine, 17 (1999) pp. 2690-2701.
Lovgren et al., The Requirement of Lipids for the Formation of Immunostimulating Complexes (Iscoms), Biotechnol. Appl. Biochem. 10:161-172 (1988).
Demana et al., "A comparison of pseudo-ternary diagrams of aqueous mixtures of Quil A, cholesterol and phospholipid prepared by lipid-film hydration and dialysis," Journal of Pharmacy and Pharmacology 56:573-580 (2004).
Copland et al., "Hydration of lipid films with an aqueous solution of Quil A: a simple method for the preparation of immune-stimulating complexes," International Journal of Pharmaceutics 196:135-139 (2000).
Kersten et al., On the structure of immune-stimulating saponin-lipid complexes (iscoms) Biochimica et Biophysica Acta, 1062:165-171 (1991).
Demana et al., "Pseudo-ternary phase diagrams of aqueous mixtures of Quil A, cholesterol and phospholipid prepared by the lipid-film hydration method," International Journal of Pharmaceutics 270:229-239 (2004).
Ozel et al., "Quaternary Structure of the Immunostimulating Complex (Iscom)," Journal of Ultrastructure and Molecular Structure Research 102:240-248 (1989).

A

B

ISCOM PREPARATION AND USE THEREOF

CROSS-REFERENCE TO RELATED APPLICATIONS

This application is a continuation of application Ser. No. 10/520,022, filed Jan. 23, 2006, which is a national stage application of International Application PCT/SE03/01180, filed on Jul. 7, 2003 and which claims priority of Swedish patent application No. 02021103, filed Jul. 5, 2002, all of which are hereby incorporated by reference.

FIELD OF INVENTION

This invention relates to a composition comprising a mixture of at least two iscom complexes or iscom matrix complexes, each complex comprising one saponin fraction from *Quillaja saponaria* Molina, and the use thereof as immunomodulators or adjuvants in formulations to be used for immunisations including vaccines. Especially the invention relates to the use of purified, semipurified or defined fractions of *Quillaja saponin* in iscom and iscom-matrix adjuvanted vaccines. The use of saponin preparations according to this invention results in products with increased tolerability and increased immunogenicity. The preparations may be used in methods to tailor the immunogenicity with increased control of inflammatory, hypersensitivity and allergic reactions.

PRIOR ART

The immune stimulatory properties of *Quillaja saponins* have been known for long (Ramon 1926) and *Quillaja saponins* have been used in free form, sometimes in combination with Al(OH)$_3$ in commercial vaccines since 1950s (Dalsgaard 1978, Ma et al. 1994, Espinet 1951). A substantially more efficient use of the *Quillaja saponins* compared to conventional free forms was described by Morein et al., in 1984—the ISCOM technology (EP 0 109 942 B1, EP 0 242 380 B1 and EP 0 180 564 B1) and a few years later the ISCOM-matrix technology (Lövgren and Morein 1988, EP 0 436 620 B1). Using the iscom technology vaccine antigens are incorporated into a 40 nm complex consisting of *Quillaja saponins*, cholesterol and phospholipid(s). The ISCOM-matrix technology employs the *Quillaja saponin*:cholesterol:phospholipid complex in mixture (not associated) with the antigen(s). Both technologies decreases or abolish the haemolytic activity of the *Quillaja saponins*, a property causing local side effects and adds to the overall toxicity of *Quillaja saponin* preparations (Bomfod et al 1992).

*Quillaja saponin* preparations are heterogeneous mixtures of surface-active glycosides and serious problems in finding/defining batches with predicted and consistent adjuvant activity led to the isolation and characterisation of a "homogenous" fraction denoted "*Quillaja saponaria* Molina" (Dalsgaard, 1974). This fraction was later shown to contain a range of related structures that were further purified into fractions/peaks by means of reversed phase HPLC (Kensil 1988, 1991, Kersten 1990 EP 0 362 279 B2, EP 0 555 276 B1). The motivation for this purification was not only to produce homogenous fractions of saponins that were readily characterised and defined but also to define a less toxic product. Acute toxicity or side effects have been major concerns for both veterinary and particularly human use of *Quillaja saponins* in vaccine preparations. These goals were only partially met with success, the purified fractions e.g., QA-21 (EP 0 362 279 B2) and combinations of fractions A and C (WO 96/11711, Iscotec-patent) were indeed chemically defined compared to "*Quillaja saponaria* Molina" but they still caused some toxicity and side effects. Despite the fact that fraction A virtually lack toxicity, a mixture consisting of 70% fraction A and 30% fraction C was not or only marginally less toxic than 100% of fraction C of *Quillaja saponaria* Molina.

In work leading to the present invention it was also shown that the different *Quillaja saponin* fractions had not only different toxicity but also different immunomodulating properties (Johansson et al., EP 0 362 279 B2). By combining these fractions different immunomodulating capacities were obtained e.g. a Th1 driving or a Th2 driving capacity. It is however desirable to reduce the side effects that limits the amount of each fraction to be used in a tolerable formulation.

SUMMARY OF THE INVENTION

The present invention relates to the use of at least two purified peaks or defined fractions of *Quillaja saponin* in iscom and iscom-matrix as separate entities (particles). I.e. these fractions are not combined in the very same iscom or iscom matrix particles, and the particles with different loads are mixed together to constitute a formulation for immunisation. It has surprisingly turned out that a mixture of iscom or iscom matrixes each comprising a different fraction of *Quillaja saponaria* Molina has lower toxicity than when these *Quillaja saponaria* Molina fractions are integrated into the same iscom or iscom matrix particle. For example the mixture of fraction A-matrix and fraction C-matrix, or the use of fraction A-matrix or fraction C-matrix alone were considerably less toxic in mice than when the same fractions were integrated in the same iscom matrix (Example 4, table 1). Further, the immunogenicity or immune modulating properties are easier to tailor, and the possibilities are considerably enhanced to make improved vaccine formulations optimised both for the target species and the needs/requirements of the vaccine antigens.

Mice are particularly sensitive to *Quillaja saponins* and overdosing leads to death within 4 days, often within 24 hours. Therefor mice were used to monitor the effects of toxicity and immunogenicity of the formulations prepared according to this invention. The interspecies variation in sensitivity to *Quillaja saponin* is huge and reflects the needs for species optimisation to obtain tolerable formulations, but also for steering to obtain optimal immunogenicity of vaccine formulations. E.g. equines do not die from large doses of *Quillaja saponin*, but they are prone to develop fever and local side effects after injection with free *Quillaja saponaria* Molina, iscoms and iscom-matrix produced from *Quillaja saponaria* Molina or mixed fractions of *Quillaja saponaria* Molina.

groups 1 through 8. Mice were bled weeks 3 and 6. The antibody responses were tested from bleeding collected at week 6.

Figure 2:
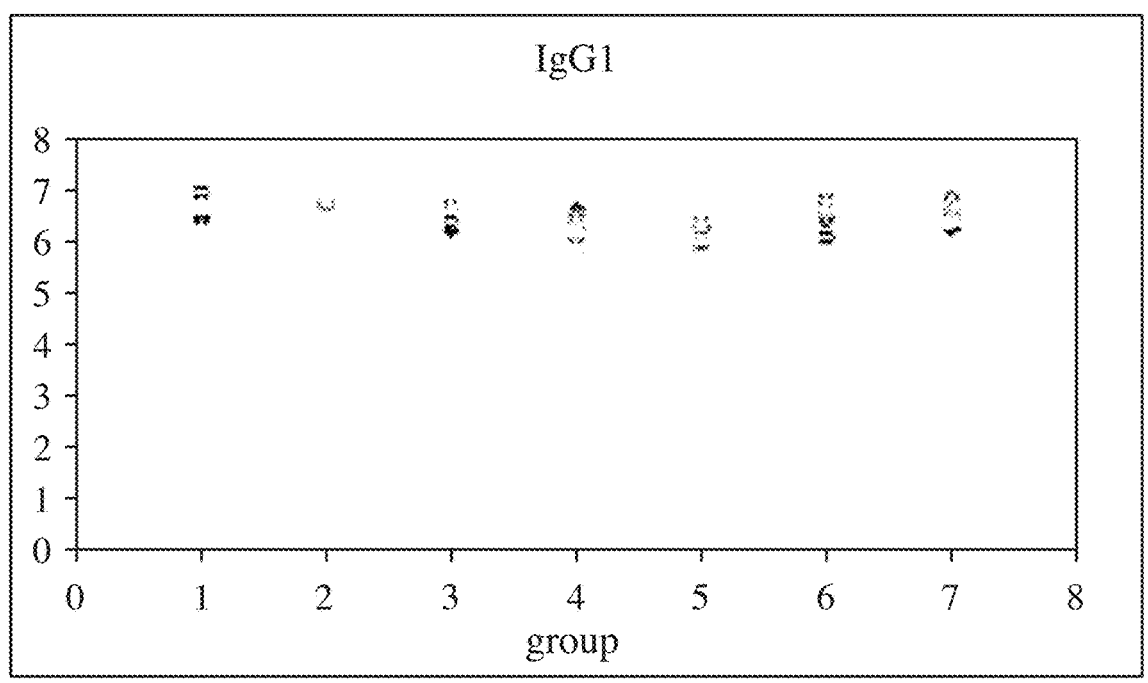
FIG. 2 shows antigen specific antibody responses against influenza virus micelles as described in the text were tested in ELISA (log Titre) in the IgG1 (A) and IgG2a (B) subclasses. Mice (female NMRI) were immunised weeks 0 and 4 with the vaccine formulations described in Table 2 i.e.
Figure 2:
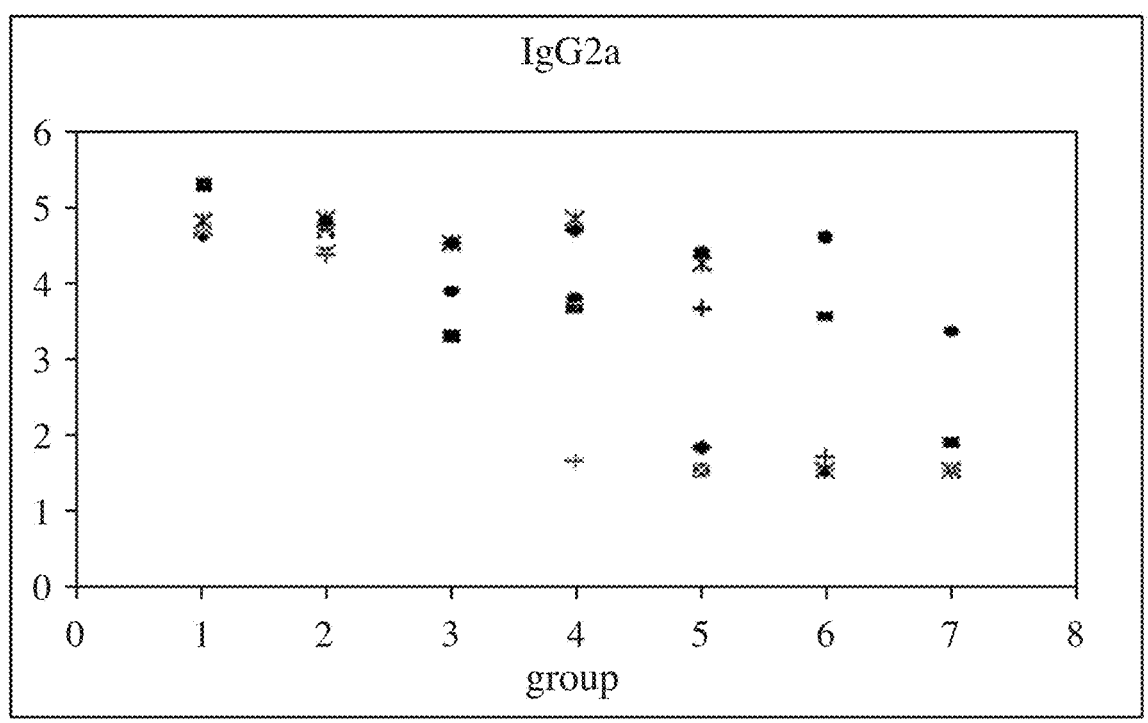
Figure 3:
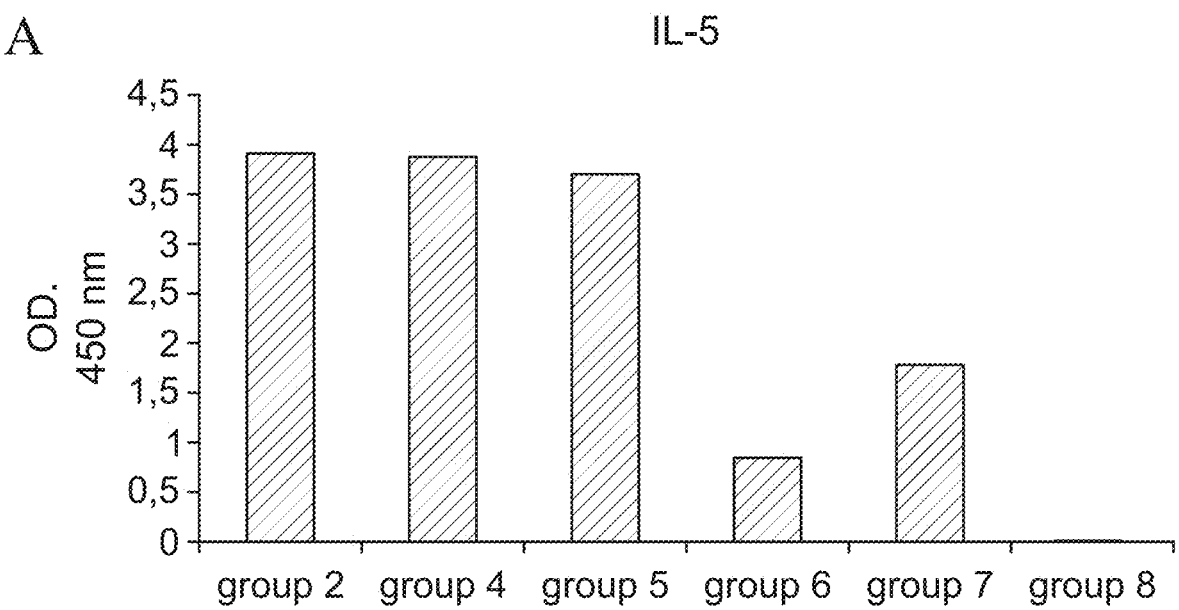
Figure 3:
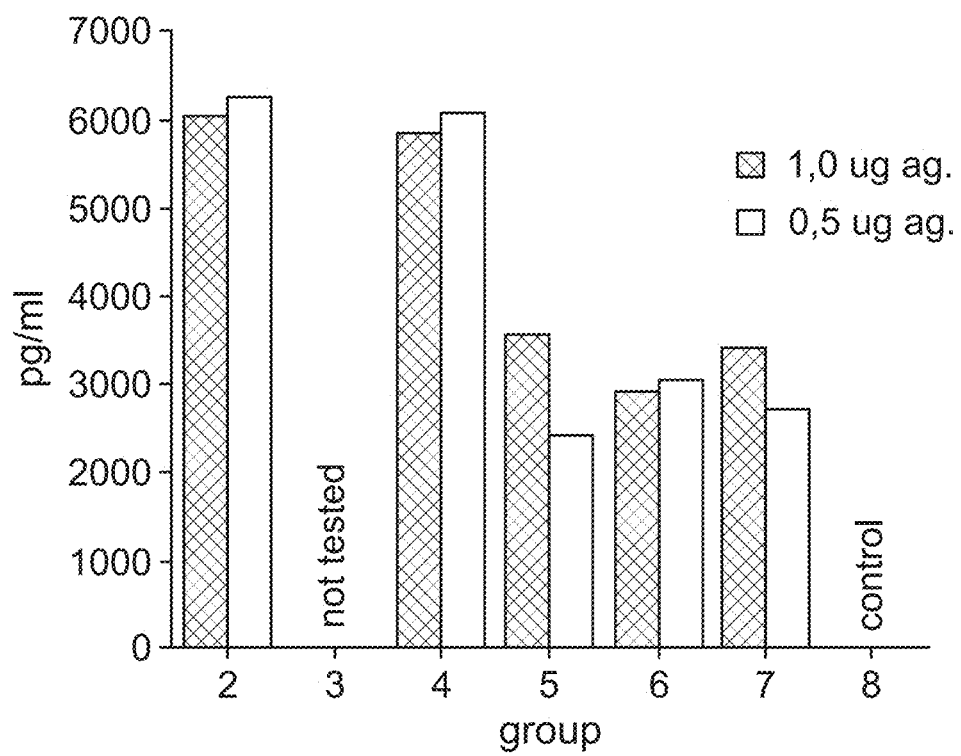

FIG. 3 shows the cell mediated immune response measured as the production of the cytokines IL-5 (A) and IFN-γ (B) by spleen cells collected week 6 after immunisation as described in FIG. 2 after stimulation in vitro with influenza virus micelles as described in the text.

Figure 4:
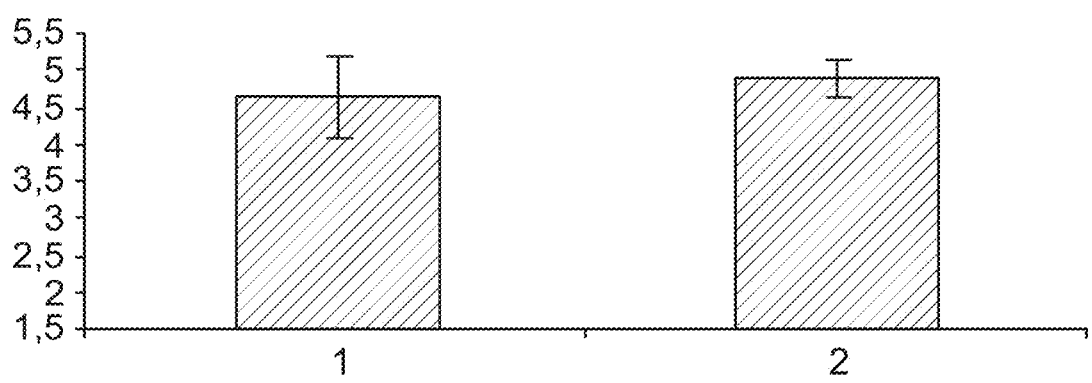
Figure 4:
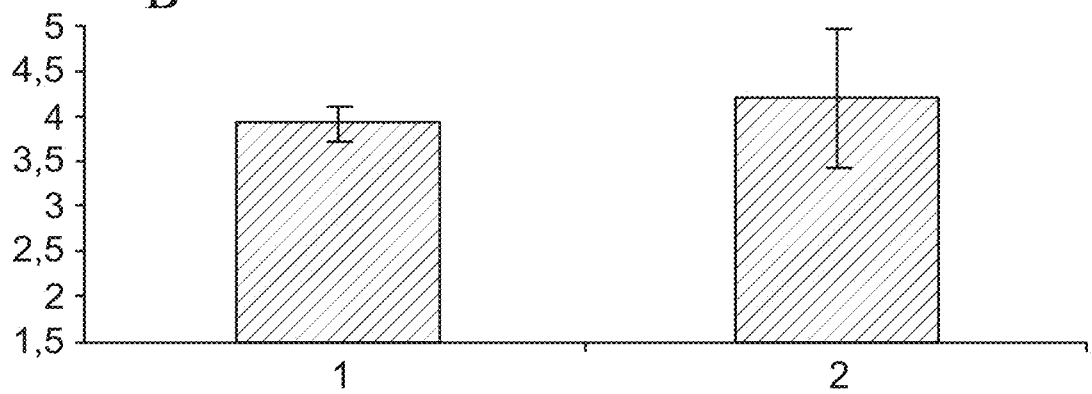

FIG. 4 shows high dose (50 µg) of QHC in matrix is toxic, while a high dose of QHA in ISCOM-MATRIX is non-toxic, when supplemented to OVA to enhance the antibody response in Balb/C mice (see text). Both formulations enhance similar specific antibody responses against OVA as measured 3 weeks after the second immunisation by ELISA for the total IgG response (A) and in the IgG2a subclass (B).

Figure 5:
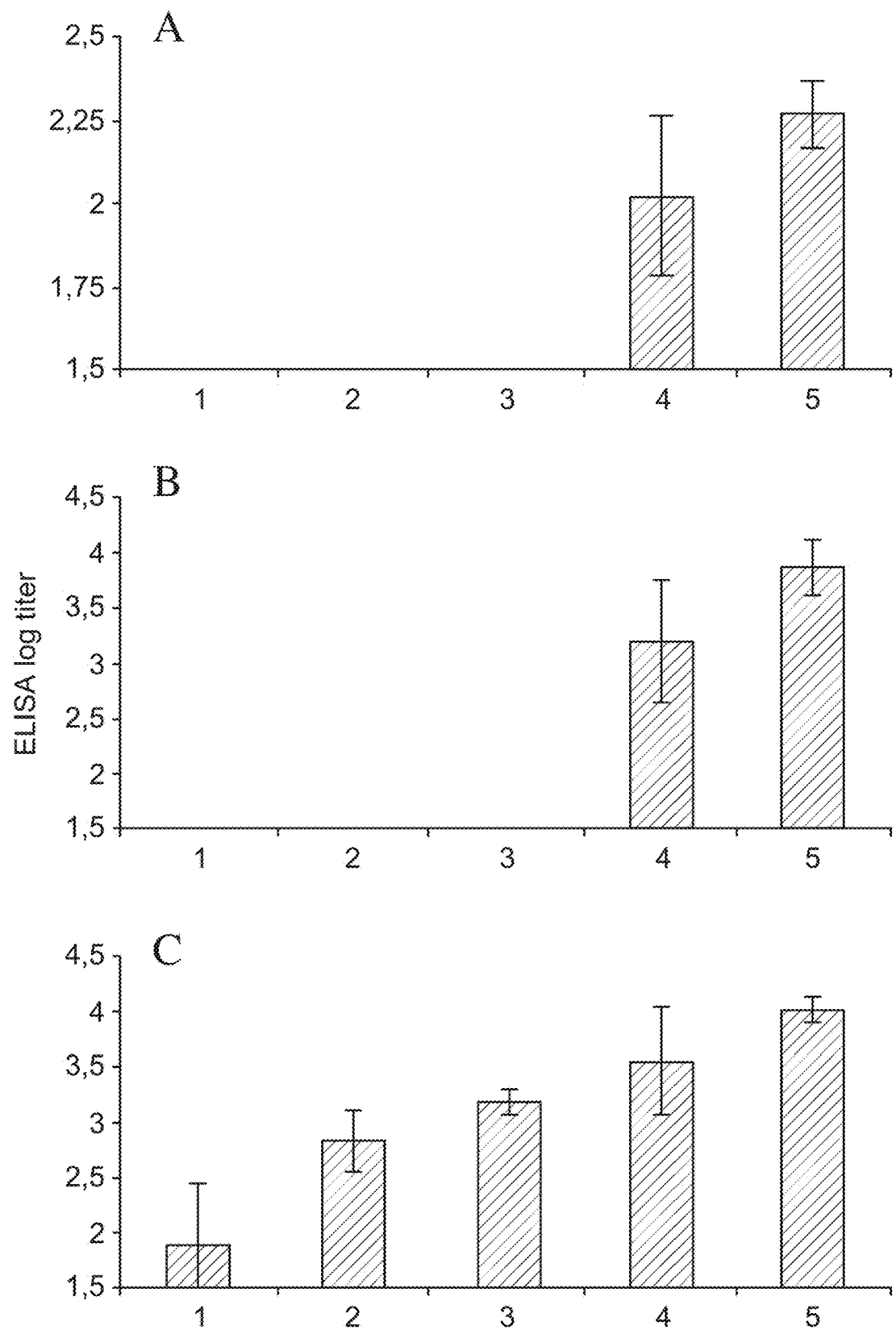

FIG. 5 shows synergistic effects of QHA and QHC matrices when supplemented to OVA to enhance the antibody response in Balb/C mice (see text). The dose of QHA and C matrices ranged as follows in group 1, no A or C; Gr. 2, 0.3 µg A no C; Gr. 3, 0.3 µg A+2 µg C; Gr. 4, 10 µg A no C; Gr. 5, 10 µg A 2 µg C. The dose of OVA was 10 µg. There were 8 mice per group, which were immunised twice 4 weeks apart s.c. with respective formulation. The antibody titres were measured by ELISA against:

A Total IgG 3 weeks after the first immunisation;
B IgG2a 2 weeks after the second immunisation; and
C IgG1 2 weeks after the second immunisation.

There is a highly significant difference between groups 4 and 5 ($p<0.0001$).

DETAILED DESCRIPTION OF THE INVENTION

The present invention relates to a composition comprising a mixture of at least two iscom complexes each complex comprising essentially one saponin fraction from *Quillaja saponaria* Molina. The iscom complex may be an iscom matrix complex or an iscom complex.

Iscom contains at least one glycoside, at least one lipid and at least one type of antigen substance. The lipid is at least a sterol such as cholesterol and optionally also phosphatidyl choline. This complex may also contain one or more other immunomodulatory (adjuvant-active) substances, and may be produced as described in EP 0 109 942 B1, EP 0 242 380 B1 and EP 0 180 564 B1.

An iscom matrix comprises at least one glycoside and at least one lipid. The lipid is at least a sterol such as cholesterol and optionally also phosphatidyl choline. The iscom complexes may also contain one or more other immunomodulatory (adjuvant-active) substances, not necessarily a saponin, and may be produced as described in EP 0 436 620 B1.

The composition according to the invention may comprise iscom or iscom matrix complexes only or mixtures of iscom complex and iscom matrix complex. Different iscom and/or iscom matrix may be mixed wherein different saponin fractions from *Quillaja Saponaria* Molina are used.

The invention also covers the use of a mixture of at least two iscom or iscom matrix complexes each comprising one saponin fraction from *Quillaja saponaria* Molina for the preparation of an immunomodulating pharmaceutical.

Another aspect of the invention is the use of a mixture of at least two iscom or iscom matrix complexes according to claim 1 each comprising one saponin fraction from *Quillaja saponaria* Molina and at least one antigen for the preparation of a vaccine.

A further aspect of the invention is the use of a mixture of at least two iscom matrix complexes according to claim 1 each comprising one saponin fraction from *Quillaja saponaria* Molina for the preparation of an adjuvant.

The immunogen which is incorporated into or associated with the iscom matrix in accordance with this invention may be any chemical entity which can induce an immune response in an individual such as (but not limited to) a human or other animal, including but not limited to a humoral and/or cell-mediated immune response to bacteria, viruses, *mycoplasma* or other micro-organisms. The specific immunogen can be a protein or peptide, a carbohydrate, polysaccharide, a lipopolysaccharide or a lipopeptide; or it can be a combination of any of these.

Particularly, the specific immunogen can include a native protein or protein fragment, or a synthetic protein or protein fragment or peptide; it can include glycoprotein, glycopeptide, lipoprotein, lipopeptide, nucleoprotein, nucleopeptide; it can include a peptide-peptide conjugate; it can include a recombinant nucleic acid expression product.

Examples of such immunogens are cited in EP 0 109 942 B1 and include, but are not limited to, those that are capable of eliciting an immune response against viral or bacterial hepatitis, influenza, diphtheria, tetanus, pertussis, measles, mumps, rubella, polio, pneumococcus, herpes, respiratory syncytial virus, haemophilias influenza, *chlamydia*, varicella-zoster virus, rabies or human immunodeficiency virus.

The antigens may be incorporated into iscom or coupled on to iscom or iscom matrix or mixed with iscom and/or iscom matrix. Any mixtures of such iscom or iscom matrix may be used. One or more antigens may be used and a transport and passenger antigen may be used as described in EP 9600647-3 (PCT/SE97/00289).

The lipids used are particularly those described in the applicant's patent EP 0 109 942 B1 in particular on p. 3 and in patent EP 0 436 620 B1 on p. 7 lines 7-24. Especially sterols such as cholesterol and phospholipids such as phosphatidylethanolamine and phosphatidylcholine are used. Lipid-containing receptors that bind to the cell-binding components, such as glycolipids including the cholera toxin's receptor, which is the ganglioside GM1, and fucosed blood group antigen may be used. The cell-binding components can then function as mucus targeting molecule and be bound to the lipid-containing substances through simply mixing them with complexes that contain them. Iscom complexes comprising such receptors and receptors are described in WO 97/30728.

The term "one saponin fraction from *Quillaja saponaria* Molina" is used throughout this specification and in the claims as a generic description of a semi-purified or defined saponin fraction of *Quillaja saponaria* or a substantially pure fraction. It is important that the fraction does not contain as much of any other fraction to negatively affect the good results that are obtained when the mixtures of iscom or iscom matrix comprising essentially one fraction is used. The saponin preparation may, if desired, include minor amounts for example up to 40% by weight, such as up to 30% by weight, up to 25% by weight, up to 20% by weight, up to 15% by weight, up to 10% by weight, up to 7% by weight, up to 5% by weight, up to 2% by weight, up to 1% by weight, up to 0.5% by weight up to 0.1% by weight of other compounds such as other saponins or other adjuvant materials.

The saponin fractions according to the invention may be the A, B and C fractions described in WO 96/11711, the B3, B4 and B4b fractions described in EP 0 436 620, the fractions QA1-22 described in EP 0 3632 279 B2, Q-VAC (Nor-Feed, AS Denmark), *Quillaja saponaria* Molina Spikoside (Isconova AB, Ultunaallén 2B, 756 51 Uppsala, Sweden).

The fractions QA-1-2-3-4-5-6-7-8-9-10-11-12-13-14-15-16-17-18-19-20-21 and 22 of EP 0 3632 279 B2, especially QA-7, 17-18 and 21 may be used. They are obtained as described in EP 0 3632 279 B2, especially at page 6 and in Example 1 on page 8 and 9.

Fractions A, B and C described in WO 96/11711 are prepared from the lipophilic fraction obtained on chromatographic separation of the crude aqueous *Quillaja Saponaria* Molina extract and elution with 70% acetonitrile in water to recover the lipophilic fraction. This lipophilic fraction is then separated by semipreparative HPLC with elution using a gradient of from 25% to 60% acetonitrile in acidic water. The fraction referred to herein as "Fraction A" or "QH-A" is, or corresponds to, the fraction, which is eluted at approximately 39% acetonitrile. The fraction referred to herein as "Fraction B" or "QH-B" is, or corresponds to, the fraction, which is eluted at approximately 47% acetonitrile. The fraction referred to herein as "Fraction C" or "QH-C" is, or corresponds to, the fraction, which is eluted at approximately 49% acetonitrile.

By combining iscom or iscom-matrix complexes comprising different fractions of *Quillaja saponaria* Molina it is possible to produce preparations that are less toxic. It has also turned out that the effect of the compositions seems to be receptor mediated i.e. to receptors on the antigen presenting cells (APC) recognising the complexes. Thus, when two different fractions of *Quillaja saponaria* Molina are integrated in the same iscom complex this complex may bind to receptors with affinity to fraction 1 plus receptors with affinity to fraction 2, i.e. two sets of receptors. Whereas when the fractions are in separate iscom particles or iscom matrix particles each particle will bind to the corresponding receptor(s) and limited to the receptors for which it has affinity. When two sets of receptors on the APC are triggered by the same particle that may cause strong effects leading to side effects. Moreover, the way that the complexes effect their action via receptors may be different in different species. Therefore, any combination of weight % of iscom complexes based on their content of different fractions of *Quillaja saponaria* Molina may be used.

The use of saponin preparations according to this invention results in products with increased tolerability, increased immunogenicity. The preparations may be used in methods to tailor the immunogenicity including increased control of inflammatory, hypersensitivity and allergic reactions. This tailor making may be species dependent and may affect toxicity, tolerability and immunogenicity.

Any ratio of subfragments of *Quillaja saponaria* Molina saponins may be used. Also, any combination of subfragments of *Quillaja saponaria* Molina may be used. Thus, two or more sub fragments may each be integrated into iscom or iscom matrix complex and used in the mixture according to the invention.

Preferably mixtures of iscom and/or matrix are used in which the fraction *Quillaja saponaria* Molina and fraction Quil C are separately incorporated into different iscom complexes or matrix. As mentioned above any combinations of weight % of the different iscom complexes based on their content of fraction A and C of *Quillaja saponaria* Molina respectively may be used. The mixtures may comprise from, 0.1 to 99.9 by weight, 5 to 95% by weight, 10 to 90% by weight 15 to 85% by weight, 20 to 80% by weight, 25 to 75% by weight, 30 to 70% by weight, 35 to 65% by weight, 40 to 60% by weight, 45 to 55% by weight, 40 to 60%, by weight, 50 to 50% by weight, 55 to 45% by weight, 60 to 40% by weight, 65 to 35% by weight, 70 to 30% by weight, 75 to 25% by weight, 80 to 20% by weight, 85 to 15% by weight, 90 to 10% by weight, 95 to 05% by weight, of iscom complexes comprising fraction A of *Quillaja saponaria* Molina (as herein defined) and the rest up to 100% in each case of interval of iscom complexes comprising fraction C of *Quillaja saponaria* Molina (as herein defined), counted on the content of the sum fractions A and C of *Quillaja saponaria* Molina in the iscom complexes.

The mixture may comprise from 75% to 99.5% by weight of fraction A and 0.5% to 25% by weight of fraction C. Preferably, the mixture comprises from 90% to 99% by weight of fraction A and 1% to 10% by weight of fraction C. A particularly preferred preparation comprises about 91% to 98% by weight of fraction A and about 2% to 9% by weight of fraction C, especially about 92% to 96% by weight of fraction A and about 4% to 8% by weight of complexes of fraction C counted on the content of the sum fractions A and C of *Quillaja saponaria* Molina in the iscom complexes.

All intervals mentioned above may be used for any combination of any fraction of *Quillaja saponaria* Molina in formulations for administration to any type of human or animal species. Examples of animal species to which the formulations according to the invention may be administrated are companion animals such as cats, dogs, horses, birds such as parrots, economical important species such as cattle, e.g. bovine species, swines, sheep, goats. Preferably more than 50% by weight of fraction C is used in combination with any of the other fractions and especially in combination with fraction A. Thus, from 50.5-99.5% by weight of C and 0.5-49.5% by weight of A may be used.

When prepared as described herein, Fractions A, B and C of *Quillaja Saponaria* Molina each represent groups or families of chemically closely related molecules with definable properties. The chromatographic conditions under which they are obtained are such that the batch-to-batch reproducibility in terms of elution profile and biological activity is highly consistent.

The present invention also extends to a vaccine composition comprising as the active component thereof either (i) an immunogenic iscom as broadly described above or (ii) an iscom matrix as broadly described above and at least one immunogen, together with one or more pharmaceutically acceptable carrier and/or diluents.

The formulation of such vaccine compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in Remington's Pharmaceutical Sciences, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

The iscom or iscom matrix complex according to the invention comprising each essentially one fraction of *Quillaja saponaria* Molina may be administrated as a mixture or separately at the same administration site or at different administration sites at the same or at different times. Different fractions of *Quillaja saponaria* Molina may be used in the different iscom complexes and matrix complexes and in the different compositions.

The invention therefore also relates to a kit of parts comprising at least two parts, wherein each part comprises one iscom complex or one iscom matrix complex each complex comprising one saponin fraction from *Quillaja saponaria* Molina. Different fractions of *Quillaja saponaria* Molina may be used in the different iscom complexes and matrix complexes in the different compositions in the different parts.

The compositions and kit of parts according to the invention may also comprise at least one other adjuvant than fractions from *Quillaja saponaria* Molina. These adjuvants may be mixed with the iscom and/or iscom matrix complexes or be integrated into the complexes.

Examples of other adjuvants that can be incorporated in the iscom and iscom matrix are any adjuvant, natural or synthetic, with desired immunomodulatory effect, e.g. muramyl dipeptide (MDP)-derivatives, such as fatty acid, substituted MDP, threonyl analogues of MDP; DDA, poly anions such as Dextran sulphate, lipopolysaccharides such as saponins (other than Quil A). ("Future prospects for vaccine adjuvants", Warren, H. S. (1988) CRC Crit. Rev. Immunol. 8:2, 83-101; "Characterisation of a non-toxic monophosphoryl lipid A", (1987) Johnson, A. G. et al, Rev. Infect. Dis. 9:5, 5512-5516; "Developmental status of synthetic immunomodulators", Berendt, M. J. et at (1985), Year Immunol. 193-201; "Immunopotentiating conjugates", Stewart-Tull, D. E., Vaccine, 85, 3:1, 40-44).

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent.

In yet another aspect, the present invention extends to a method of eliciting or inducing an immune response in an individual, which comprises administering to the individual an immunologically effective amount of a vaccine composition as broadly described above.

As previously mentioned, the individual may be a human or other animal, including a livestock animal (e.g. sheep, cow or horse), laboratory test animal (e.g. mouse, rat, rabbit or guinea pig), companion animal (e.g. dog or cat) or wild animal.

An immunologically effective amount means that amount necessary at least partly to attain the desired immune response, or to delay the onset of, inhibit the progression of, or halt altogether, the onset or progression of the particular condition being treated. This amount varies depending upon the health and physical condition of the individual to be treated, the taxonomic group of individual to be treated, the capacity of the individual's immune system to synthesise antibodies, the degree of protection desired the formulation of the vaccine, the assessment of the medical situation, and other relevant factors. It is expected that the amount will fall in a relatively broad range that can be determined through routine trials.

Throughout this specification and the claims which follow, unless the context requires otherwise, the word "comprise", or variations such as "comprises" or "comprising", will be understood to imply the inclusion of a stated component or group of components but not the exclusion of any other components or group of components.

All publication mentioned herein are hereby incorporated as reference. The invention will now be described by the following non-limiting examples.

Example 1

Preparation of *Quillaja saponaria* Molina Subfragment Saponins

Purification of crude *Quillaja saponaria* Molina extract to fractions A, B and C. A solution (0.5 ml) of crude *Quillaja* bark extract in water (0.5 g/ml) is pre-treated on a sep-pak column (Waters Associates, MA).

The pre-treatment involves washing of the loaded sep-pak column with 10% acetonitrile in acidic water in order to remove hydrophilic substances. Lipophilic substances including QH-A, QH-B and QH-C are then eluted by 70% acetonitrile in water.

The lipophilic fraction from the sep-pak column is then separated by a semipreparative HPLC column (CT-sil, C8, 10×250 mm, ChromTech, Sweden). The sample is eluted through the column by a gradient from 25% to 60% acetonitrile in acidic water. Three fractions are collected from the HPLC column during the separation. The residues after evaporation of these three fractions constitute QH-A, QH-B and QH-C.

Figure 1:
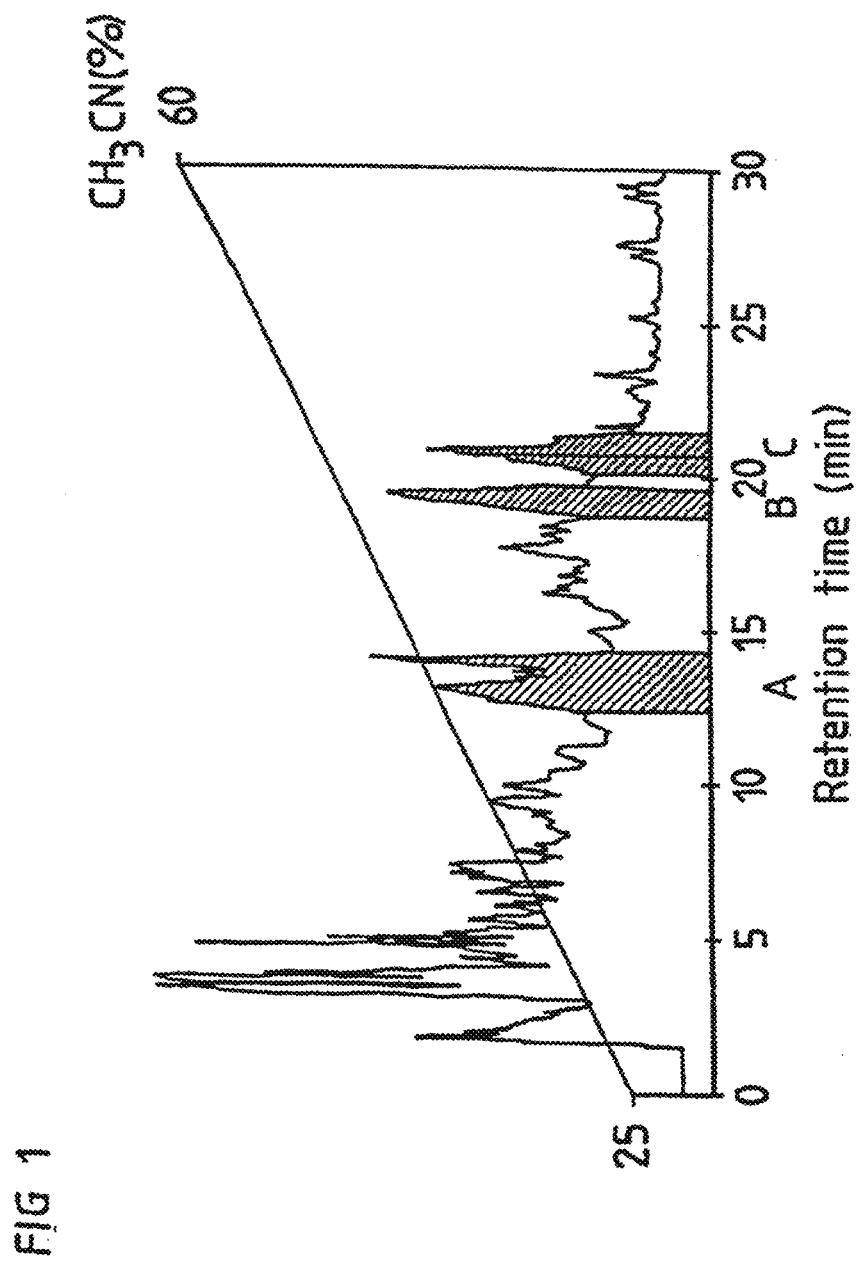
FIG. 1 shows the preparation of fractions A, B and C by HPLC.

The fractions designated QH-A, QH-B and QH-C were eluted at approximately 39, 47 and 49% acetonitrile respectively. The exact elution profile and conditions are shown in FIG. 1.

Example 2

Preparation of Iscom Matrix

Materials:
Cholesterol, e.g., Sigma C 8503
Phosphatidyl choline (egg derived) e.g., Sigma P 3556
MEGA-10 (Bachem AG, Switzerland)
*Quillaja saponin* fractions A and C (patent W09611711)
0.22 µm Sterile filters (Acrodisc)
PBS (10 mM phosphate buffered 150 mM saline, pH 6.8-7.4)
Slide-A-Lyzer cassettes MW cut off 12-14.000 (Pierce)
MEGA-10 (stock solution):
Make a 20% (w/w) stock solution by adding 8 ml distilled water to 2.0 g of dry solid MEGA-10. Dissolve by gentle heating (30-50° C.). Filter through a 0.22 nm sterile filter, aliquot and store at 20° C.
Lipid Mixture (15 mg/ml):
Dissolve 100 mg of each cholesterol and phosphatidyl choline in 10 ml 20% MEGA-10. The lipids dissolve slowly at 30-60° C. with slow stirring. Filter through a 0.22 nm sterile filter, aliquot and store at −20° C. After freezing, the lipid mixtures need to be heated up to 40° C. until clear. Temperate all solutions to 24±1° C.
Saponin Stock Solutions (100 mg/ml):
1.0 gram of *Quillaja saponaria* Molina fractions (A or C is dissolved in sterile distilled water. Keep aliquots frozen at −20° C.). Filter through a 0.22 run sterile filter, aliquot and store at −20° C.

The different iscom-matrix is preparations are produced as outlined in Table 1.
Prepare the mixtures as follows.
Add 2 ml PBS to a 50 ml falcon tube
1 Add the lipid mixture and mix thoroughly
2 Add saponin and mix thoroughly 3 Add PBS to a final volume of 12.0 ml, mix thoroughly
4 Incubate for 30 minutes
5 Fill into Slide-A-Lyzer
6 Dialyse against 4 changes of 2 liters of PBS (24±1° C.) (for 48-60 hours)
7 Aspirate from Slide-A-Lyzer and filter through 0.22 nm sterile filter.

The formation of iscom-matrix was verified by negative staining electron microscopy and the resulting concentrations of *Quillaja* saponin was determined by HPLC.

TABLE 1

| Preparation | Lipid-mixture | | *Quillaja* saponin | | PBS |
| | Amount (mg) | Volume (µl) | Amount (mg) | Volume (µl) | Volume (ml) |
| --- | --- | --- | --- | --- | --- |
| A-matrix | 12 | 800 | 48 | 480 | 2.0 + 8.72 |
| C-matrix | 12 | 800 | 30 | 300 | 2.0 + 8.90 |
| 703-matrix | 12 | 800 | 42 | 420 | 2.0 + 8.78 |

Example 3

Preparation of PR-8 Protein Micelles

1 Dilute 12 mg of PR-8 monomers (1.5 mg/ml) with PBS to a final protein concentration of 1.0 mg/ml.
2 Filter through 0.22 nm sterile filter
3 Fill into Slide-A-lyzer
4 Dialyse against 4 changes of 2 liters of PBS (24±1° C.) (for 48-60 hours)
5 Aspirate from Slide-A-Lyzer Example 4

Immunisation Study

This example was carried out to show in a comparative study that iscom-matrix composed of a mixture matrix particles provokes minimal degree of side effects. One set of particles contain QHA as the only saponin and the other set of particles contain QHC as the only saponin and were prepared according to Example 2. This formulation is named matrix with a "mixture of particles". The comparison is done with an iscom matrix as described in Paten WO 96/11711 i.e. each particle contain both QHA and QHC in e.g. a ratio of 70% QHA and 30% of QHC. This is a matrix with all in one particle.

Balb/C mice were immunised days 0 and 42 with 1 µg of PR8 micelles (prepared as described in example 3) mixed with the iscom matrix formulation matrix with a mixture of particles and compared with the iscom matrix with all in one particle, or with iscom matrix containing 100% QHA or 100% QHC as described in Table 2. Groups in which more than 50% of the mice died or suffered from unacceptable side effects by the treatment were culled and excluded from further investigations.

Serum samples were taken from all mice in groups 1-7 day 56, two weeks after the booster administration. The sera were screened for antigen specific antibodies of IgG 1 (A) and IgG2a (B) subclasses. Group 8 in the figure represents unvaccinated mice. The results are shown in FIG. 2.

After the second bleeding spleens were taken from two mice per group (groups 2, 4, 5, 6 and 7). The spleen cells were stimulated with PR8 micelles in vitro and the antigen specific induction of IL-5 (A) and IFN-γ (B) was measured. Group 8 in the figure represents unvaccinated mice. The results are shown in FIG. 3.

TABLE 2

Balb/C mice were immunised days 0 and 42 with the iscom matrix formulation matrix with a mixture particles (MIX groups 1, 2, and 3) and compared with, the iscom matrix with all in one particle (CONV groups 7, 8, 9, 10 and 11), or with iscom matrix containing 100% QHA (groups 4 and 5) or 100% QHC (group 6 and 12).

| Group no | Amount (µg) | A:C (ratio) | MIX/CONV | No of mice | Dead#/total |
| --- | --- | --- | --- | --- | --- |
| 1 | 50 | 80:20 | MIX | 8 | 2/8 |
| 2 | 50 | 92:8 | MIX | 8 | 0/8 |
| 3 | 50 | 96:4 | MIX | 8 | 0/8 |
| 4 | 50 | 100% A | | 8 | 0/8 |
| 5 | 10 | 100% A | | 8 | 0/8 |
| 6 | 10 | 100% C | | 8 | 0/8 |
| 7 | 10 | 70:30 | CONV | 8 | 0/8 |
| 8 | 50 | 80:20 | CONV | 8 | 8/8 |
| 9 | 50 | 92:8 | CONV | 8 | 6/8 |
| 10 | 50 | 96:4 | CONV | 8 | 5/8 |
| 11 | 50 | 70:30 | CONV | 8 | 8/8 |
| 12 | 50 | 100% C | | 8 | 8/8 |

Mice that were euthanized or died within 24 h after administration.
A:C ratio (weight) of *quillaja* saponin fraction A and C Results Mice immunised PR8 micelles adjuvanted with high dose (50 µg) of iscom matrix containing 80% QHA and 20% of QHC i.e. 10 µg died within 1 or 2 days. Likewise did mice immunised with 50 µg of the formulation 100% QHC died within 2 days.

In contrast mice immunised with 50 µg of the formulation 100% QHA survive without any noticed adverse reactions. I.e. the lower dose of QHC was sufficient to kill mice when incorporated in the same matrix particle as QHA (CONV group 8 in Table 2). Even when a low amount as 4 µg (8(%) of QHC in combination with 46 µg (92%) of QHA in a CONV matrix killed 6 out of 8 mice (group 9 Table 2). Also 2 µg (4%) QHC killed mice when combined with QHA in CONV matrix (group 10 Table 2). Mice in group 6 (Table 2) received 10 µg QHC being 100% (i.e. no QHA) in the matrix and all mice survived.

Thus, the mice were more sensitive to QHC when combined with QHA in the same CONV matrix particle (groups 8, 9, and 10).

Mice receiving low dose matrix i.e. 10 µg of total saponin divided on 70% of QHA and 30% of QHC survived all. In this case the mice received 3 µg QHC.

Mice immunised with PR8 micelles adjuvanted with a formulation containing different matrix particles i.e. a mixture of particles (MIX) including one set of QHA and one set of QHC survived much higher doses of this matrix formulation than the CONY formulation. Mice injected with the formulation with 92% QHA (46 µg) and 8% QHC (4 µg) group 2 in Table 2 (92:8) or with the formulation 96:4 (Group 3 in Table 2) containing 2 µg of QHC survived all. This outcome shall be compared with that of corresponding amounts of QHA and QHC in CONV matrix (groups 9 and 10 Table 2) which caused high mortality.

Thus, mortality-toxicity can be avoided by physical separation of QHC from QHA and distribute them into different matrix particles.

Enhancement of Antibody Response

The results are shown in FIG. 2. Antigen specific response divided into IgG subclasses. Mice (female NMRI) were immunised weeks 0 and 4 with the vaccine formulations described in Table 2. Mice were bled weeks 3 and 6. The IgG1 ($^{10}$ log Elisa titres) response at week 6 is shown in A and the corresponding IgG2 response in B.

An important finding in this experiment is that the immune enhancing capacity is retained or enhanced as measured by antibody responses when QHA and QHC are separated into different sets of particles, as demonstrated in FIG. 2.

In FIG. 2 it is shown that a mixture of particles (MIX) enhance the same level of IgG1 antibody (FIG. 2A) to PR8 micelles as the same dose of QHA and QHC in the same proportions when incorporated in the same particle i.e. CONV particles. However, higher levels of IgG2a antibody antibodies were enhanced by the MIX formulation (FIG. 2B). The groups 2 and 3 (MIX) shall be compared with the groups 9 and 10 (CONV) QHA-QHC matrix and with 100% of low dose QHC matrix (group 6) and with 100% of QHA high dose matrix (group 4 Table 2). Mice in group 7 injected with a low dose of 10 µg (CONV 70:30), i.e. the dose the mice can accept, responded with a potent IgG1 (FIG. 2A) response, but a low IgG2a response (FIG. 2B).

Thus, the invention with a matrix formulation with a mixture of matrix particles can be given in high doses evading side effects, enhance the antibody response to higher levels than those with than the CONV matrix. Particularly the IgG2a response is enhanced. The IgG2a response is e.g. particularly important for defense against intracellular parasites e.g. viruses.

Enhancement of Cell Mediated Immune Response

The CONV matrix formulations have inferior capacity to enhance cell mediated immunity in the doses tolerated than the MIX formulations (FIGS. 3 A and B). The MIX formulation (92:8, group 2) enhance considerably higher IL-5 levels than the CONV (70:30 group 7), QHA-QHC formulation, or the 100% QHC matrix. Formulation (group 6). The mix (92:8, group 9) formulation also enhances the IFN-γ considerably better than the QHC 100% matrix (group 6) or the CONV (70:30, group 7) formulation.

To note is that QHA has a strong capacity to enhance cell mediated immune responses measured by IL-5 and IFN-γ production, but a low capacity to enhance antibody response.

In conclusion the invention defines a concept for iscom and iscom matrix formulations that considerably reduce toxicity and side effects allowing potent doses of the adjuvant active molecules without loosing capacity to enhance immune response.

Moreover, while a low but acceptable dose of a QHC matrix formulation has good capacity to enhance and IgG1 response it is lower with regard to the important IgG2a response. The capacity of QHC matrix to induce cell mediated immunity is also comparatively low to that of the invention.

The QHA matrix potently enhances cell mediated immunity, but is inferior to the invention to enhance antibody mediated immunity.

The invention with mixed matrix particles is superior to matrix formulations containing QHA and QHC in the same particle (CONY) measured by IgG2a antibody response and measured by cell mediated responses.

The new invention enhances a complete immune response and is therefore superior to the earlier described matrix formulations, which this example 4 shows.

Example 5

In this experiment it is emphasised that that QHA is well tolerated and has a strong immune enhancing and immune modulatory capacity. Ovalbumin (OVA) is used because it is a weak antigen and as such it does not induce a Th1 type of response. QHA is compared with QHC, since the latter is evaluated in human clinical trial.

Materials and Methods

Preparation of *Quillaja saponaria* Molina sub fragments is described in EXAMPLE 1.

Preparation of Iscom matrix is described in EXAMPLE 2.

Experimental Design

Group 1 consisted of 8 mice immunised twice 4 weeks apart subcutaneously (s.c.) with 10 µg OVA adjuvanted with 50 µg QHA. Group 2 had the same number of mice immunised by the same procedure but the adjuvant was 50 µg QHC.

The shown antibody responses are from sera collected 2 weeks after the boost.

Antibody Determination

The specific OVA serum antibody responses were determined by ELISA both for total IgG response and in the IgG2a subclasses as described in EXAMPLE 4 using a standard procedure with 10 µg of OVA per ml for coating the ELISA plates as test antigen.

Results

All mice immunised with OVA adjuvanted with QHA matrix survived and did not develop any sign of discomfort. Out of 8 mice immunised with OVA adjuvanted with QHC matrix 4 mice died i.e. 50%.

There is no significant difference between the groups with regard total antibody responses (FIG. 4 A), but the ELISA titres varied more between the animals in group 1, i.e. mice immunised with QHA.

There was no difference in mean titres in the IgG2a subclass between group 1 and 2 except that the ELISA titres varied more between individual animals in group 2 i.e. mice immunised with QHC (FIG. 4 B).

In the second experiment of this example it was explored whether QHA matrix can benefit from the complementation with another adjuvant. The dose of QHA matrix and C matrix ranged as follows in group 1, no A or C; Gr. 2, 0.3 µg A no C; Gr. 3, 0.3 µg A+2 µg C; Gr. 4, 10 µg A no C; Gr. 5, 10 µg A 2 µg C. The dose of OVA was 10 µg. There were 8 mice per group, which were immunised twice 4 weeks apart s.c. with respective formulation. (FIGS. 5 A, B and C).

Sera were collected 3 weeks after the first immunisation and 2 weeks after the boost.

The specific OVA serum antibody responses were determined by ELISA for total IgG response and in the IgG2a and IgG 1 subclasses as described (Johansson, M and Lövgren-Bengtsson (1999) Iscoms with different *Quillaja saponin* components differ in their immunomodulating activities. Vaccine 19, 2894-2900).

Results

After the first immunisation no antibody response was recorded in mice receiving non-adjuvanted OVA or OVA adjuvanted with 0.3 µg of QHA matrix with and without 2 µg of QHC matrix (FIG. 5A).

After the second immunisation a low response was detected in 3 out of 8 mice immunised with non-adjuvanted OVA in the IgG 1 subclass but no response was recorded in the IgG2a subclass. Neither was antibody responses recorded with the lowest adjuvant doses of QHA matrix i.e. 0.3 µg with and without 2 µg of QHC matrix. There was a clear enhancement of the antibody response in the IgG2a subclass when the low dose of 2 µg QHC was added to the 10 µg of QHA (FIG. 5B).

CONCLUSION

QHA MATRIX has a very low toxicity and still a strong modulatory effect, when included in ISCOMATRIX as shown by promoting a strong TH1 type of response, in contrast to the non-adjuvanted or the very low adjuvanted OVA, which only elicited antibody response in the IgG 1 subclass. It is also shown that the QHA matrix synergies with a low dose of QHC matrix. These results are important, because it makes it possible to optimise the adjuvant effect and minimise the side effects in a simple manner. As shown for a weak antigen as OVA requiring potent adjuvant.

REFERENCES

Bomford, R, Stapleton, M., Winsor, S., Beesley, J. E., Jessup, E. A., Price, K. R. and Fenwick, G. R. (1992). Adjuvanticity and iscom formation by structurally diverse saponins Vaccine 10, 572-577.

Cox, J. C. and Coulter, A. R. (1992), "Advances in Adjuvant Technology and Application", in Animal Parasite Control Utilising Biotechnology, Chapter 4, Ed. Yong, W. K. CRC Press.

Dalsgaard, K. (1974), Arch. Gesamte Virusforsch, 44, 243.

Dalsgaard, K. (1978). A study on the isolation and characterisation of the saponin *Quillaja saponaria* Molina. Evaluation of its adjuvant activity with special reference to the application in foot-and-mouth disease. Acta Vet. Scand. 69 (Suppl.), 1-40.

Espinet, R. G. (1951). Nuevo tipo de vacuna antiafosa a complejo glucovirico. Gac. Vet. 74, 1-13.

Johansson, M., Lövgren-Bengtsson, K. (1999) Iscoms with different *Quillaja saponin* components differ in their immunomodulating activities. Vaccine. 17, 2894-2900.

Kensil, C. A., et al. (1988), International Patent Application No. PCT/US88101842.

Kensil, C. A. et al. (1991), J. Immunol., 146, 431.

Kersten, G. F. A. et al. (1990). "Aspects of Iscoms. Analytical, Pharmaceutical and Adjuvant Properties; Thesis, University of Utrecht.

Lövgren, K. and Morein, B. (1988). The requirement of lipids for the formation of immunostimulating complexes (iscoms). Biotechnol. Appl. Biochem. 10, 161-172.

Ma, J., Bulger, P. A., Davis, D. R., Perilli-Palmer, P., Bedore, D. A., Kensil, C. R., Young, E. M., Hung, C. H., Seals, J. R. and Pavia, C. S. (1994). Impact of the saponin adjuvant QS-21 and aluminium hydroxide on the immunogenicity of recombinant OspA and OspB of *Borrelia burgdorferi*. Vaccine 12, 925-932.

Ramon, G. (1926). Procédés pour accroitre la production des antitoxines. Ann. Inst. Pasteur, Paris 40, 1-10.

The invention claimed is:

1. A composition comprising at least two iscom particles, wherein:
the first iscom particle comprises fraction A of *Quillaja saponaria* Molina and not fraction C of *Quillaja saponaria* Molina; and
the second iscom particle comprises fraction C of *Quillaja saponaria* Molina and not fraction A of *Quillaja saponaria* Molina.

2. The composition of claim 1, wherein fraction A of *Quillaja saponaria* Molina and fraction C of *Quillaja saponaria* Molina account for 50% to 70% by weight and 50% to 30% by weight, respectively, of the sum of weights of fraction A of *Quillaja saponaria* Molina and fraction C of *Quillaja saponaria* Molina in the composition.

3. The composition of claim 1, wherein fraction A of *Quillaja saponaria* Molina and fraction C of *Quillaja saponaria* Molina account for 30% to 50% by weight and 70% to 50% by weight, respectively, of the sum of weights of fraction A of *Quillaja saponaria* Molina and fraction C of *Quillaja saponaria* Molina in the composition.

4. The composition of claim 1, wherein fraction A of *Quillaja saponaria* Molina and fraction C of *Quillaja saponaria* Molina account for 75% to 99.5% by weight and 25% to 0.5% by weight, respectively, of the sum of weights of fraction A of *Quillaja saponaria* Molina and fraction C of *Quillaja saponaria* Molina in the composition.

5. The composition of claim 1, wherein fraction A of *Quillaja saponaria* Molina and fraction C of *Quillaja saponaria* Molina account for 90% to 99% by weight and 10% to 1% by weight, respectively, of the sum of weights of fraction A of *Quillaja saponaria* Molina and fraction C of *Quillaja saponaria* Molina in the composition.

6. The composition of claim 1, wherein fraction A of *Quillaja saponaria* Molina and fraction C of *Quillaja saponaria* Molina account for 91% to 98% by weight and 9% to 2% by weight, respectively, of the sum of weights of fraction A of *Quillaja saponaria* Molina and fraction C of *Quillaja saponaria* Molina in the composition.

7. The composition of claim 1, wherein fraction A of *Quillaja saponaria* Molina and fraction C of *Quillaja saponaria* Molina account for 92% to 96% by weight and 8% to 4% by weight, respectively, of the sum of weights of fraction A of *Quillaja saponaria* Molina and fraction C of *Quillaja saponaria* Molina in the composition.

8. The composition of claim 1, wherein fraction A of *Quillaja saponaria* Molina and fraction C of *Quillaja saponaria* Molina account for 0.1% to 99.9% by weight and 99.9% to 0.1% by weight, respectively, of the sum of weights of fraction A of *Quillaja saponaria* Molina and fraction C of *Quillaja saponaria* Molina in the composition.

9. The composition of claim 1, wherein fraction A of *Quillaja saponaria* Molina and fraction C of *Quillaja saponaria* Molina account for 5% to 95% by weight and 95% to 5% by weight, respectively, of the sum of weights of fraction A of *Quillaja saponaria* Molina and fraction C of *Quillaja saponaria* Molina in the composition.

10. The composition of claim 1, wherein the first iscom particle is selected from the group consisting of iscom matrix complex particle and iscom complex particle.

11. The composition of claim 1, wherein the second iscom particle is selected from the group consisting of iscom matrix complex particle and iscom complex particle.

12. The composition of claim 1, wherein the composition has a lower toxicity than a corresponding composition in which corresponding amounts of fraction A of *Quillaja saponaria* Molina and fraction C of *Quillaja saponaria* Molina are integrated together in iscom particles of the corresponding composition instead of separately in the first and second iscom particles.

13. A composition comprising at least two iscom particles, wherein: the first iscom particle consists essentially of fraction A of *Quillaja saponaria* Molina; the second iscom particle consists essentially of fraction C of *Quillaja saponaria* Molina; and the composition has a lower toxicity than a corresponding composition in which corresponding amounts of fraction A of *Quillaja saponaria* Molina and fraction C of *Quillaja saponaria* Molina are integrated together in iscom particles of the corresponding composition instead of separately in the first and second iscom particles.

14. The composition of claim 13, wherein fraction A of *Quillaja saponaria* Molina and fraction C of *Quillaja saponaria* Molina account for 50% to 70% by weight and 50% to 30% by weight, respectively, of the sum of weights of fraction A of *Quillaja saponaria* Molina and fraction C of *Quillaja saponaria* Molina in the composition.

15. The composition of claim 13, wherein fraction A of *Quillaja saponaria* Molina and fraction C of *Quillaja saponaria* Molina account for 30% to 50% by weight and 70% to 50% by weight, respectively, of the sum of weights of fraction A of *Quillaja saponaria* Molina and fraction C of *Quillaja saponaria* Molina in the composition.

16. The composition of claim 13, wherein fraction A of *Quillaja saponaria* Molina and fraction C of *Quillaja saponaria* Molina account for 75% to 99.5% by weight and 25% to 0.5% by weight, respectively, of the sum of weights of fraction A of *Quillaja saponaria* Molina and fraction C of *Quillaja saponaria* Molina in the composition.

17. The composition of claim 13, wherein fraction A of *Quillaja saponaria* Molina and fraction C of *Quillaja saponaria* Molina account for 90% to 99% by weight and 10% to 1% by weight, respectively, of the sum of weights of fraction A of *Quillaja saponaria* Molina and fraction C of *Quillaja saponaria* Molina in the composition.

18. The composition of claim 13, wherein fraction A of *Quillaja saponaria* Molina and fraction C of *Quillaja saponaria* Molina account for 91% to 98% by weight and 9% to 2% by weight, respectively, of the sum of weights of fraction A of *Quillaja saponaria* Molina and fraction C of *Quillaja saponaria* Molina in the composition.

19. The composition of claim 13, wherein fraction A of *Quillaja saponaria* Molina and fraction C of *Quillaja saponaria* Molina account for 92% to 96% by weight and 8% to 4% by weight, respectively, of the sum of weights of fraction A of *Quillaja saponaria* Molina and fraction C of *Quillaja saponaria* Molina in the composition.

20. The composition of claim 13, wherein fraction A of *Quillaja saponaria* Molina and fraction C of *Quillaja saponaria* Molina account for 0.1% to 99.9% by weight and 99.9% to 0.1% by weight, respectively, of the sum of weights of fraction A of *Quillaja saponaria* Molina and fraction C of *Quillaja saponaria* Molina in the composition.

21. The composition of claim 13, wherein fraction A of *Quillaja saponaria* Molina and fraction C of *Quillaja saponaria* Molina account for 5% to 95% by weight and 95% to 5% by weight, respectively, of the sum of weights of fraction A of *Quillaja saponaria* Molina and fraction C of *Quillaja saponaria* Molina in the composition.

22. The composition of claim 13, wherein the first iscom particle is selected from the group consisting of iscom matrix complex particle and iscom complex particle.

23. The composition of claim 13, wherein the second iscom particle is selected from the group consisting of iscom matrix complex particle and iscom complex particle.

24. A method of immunization comprising administering the composition of claim 1 to a human or an animal.

25. The method of claim 24, wherein:
the composition has a lower toxicity than a corresponding composition in which corresponding amounts of fraction A of *Quillaja saponaria* Molina and fraction C of *Quillaja Saponaria* Molina are integrated together in iscom particles of the corresponding composition instead of separately in the first and second iscom particles; and
the administration enhances cell-mediated and antibody responses in the human or the animal in comparison to administering the corresponding composition.

26. A method of immunization comprising administering the composition of claim 13 to a human or an animal.

* * * * *